United States Patent [19]

Singh et al.

[11] Patent Number: 5,436,263
[45] Date of Patent: Jul. 25, 1995

[54] INHIBITORS OF FARNESYL-PROTEIN TRANSFERASE

[75] Inventors: Sheo B. Singh, Edison, N.J.; Barry A. Katz, Chapel Hill, N.C.; Russell B. Lingham, Watchung, N.J.; Isabel Martin, Madrid, Spain; Keith C. Silverman, Somerset, N.J.

[73] Assignee: Merck & Co., Inc., Rahway, N.J.

[21] Appl. No.: 216,110

[22] Filed: Mar. 22, 1994

[51] Int. Cl.[6] .................. A61K 31/335; C07D 313/00
[52] U.S. Cl. .................. 514/450; 549/354; 435/254.1
[58] Field of Search .................. 549/354; 514/450

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,245,061 | 9/1993 | Singh | 554/121 |
| 5,256,399 | 10/1993 | Sessler | 424/9 |
| 5,260,465 | 11/1993 | Singh et al. | 560/190 |
| 5,260,479 | 11/1993 | Singh | 568/821 |
| 5,276,217 | 1/1994 | Tius | 568/821 |
| 5,326,773 | 7/1994 | De Solms | 514/336 |
| 5,340,828 | 8/1994 | Graham | 514/357 |
| 5,352,705 | 10/1994 | Deana | 514/630 |

FOREIGN PATENT DOCUMENTS

| | | |
|---|---|---|
| 0456180A1 | 11/1991 | European Pat. Off. . |
| 0537007A1 | 4/1993 | European Pat. Off. . |
| 91/16340 | 10/1991 | WIPO . |

OTHER PUBLICATIONS

Kohl, N. E. et al., "Protein farnesyltransferase inhibitors block the growth of ras–dependent tumors in nude mice", Proc. Natl. Acad. Sci., USA, vol. 91, pp. 9141–9145, (1994).
Bos, J. L., ras Oncogenes in Human Cancer: A Review, (1989), Cancer Research, 49, pp. 4682–4689.
Gibbs, J. B., Ras C-Terminal Processing Enzymes–New Drug Targets?, (1991), Cell, 65, 1–4.
Gibbs, J. B. et al., Selective Inhibition of Farnesyl–Protein Transferase Blocks Ras Processing in Vivo, (1993), The Journal of Biol. Chemistry, 268, No. 11, pp. 7617–7620.
Goldstein, J. S., et al., Journal of Biological Chemistry, vol. 266, No. 24, pp. 15575–15578 (1991).
James, G. L. et al., Benzodiazepine Peptidomimetics: Potent Inhibitors of Ras Farnesylation in Animal Cells, (1993), Science, 260, pp. 1937–1942.
Kohl, N. E. et al., Selective Inhibition of ras–Dependent Transformation by a Farnesyltransferase Inhibitor, (1993), Science, 260, pp. 1934–1937.
Leftheris, K. et al., Peptide Based P21RAS Farnesyl Transferase Inhibitors: Systematic Modification of the Tetrapeptide CA1A2X Motif, (1994), Bioorganic & Medicinal Chemistry Letters, 4, No. 7, pp. 887–892.
Pompliano, D. L. et al., Steady-State Kinetic Mechanism of Ras Farnesyl: Protein Transferase, (1992), Biochemistry, 31, pp. 3800–3807.
Qian, Y. et al., Design and Structural Requirements of Potent Peptidomimetic Inhibitors of p21ras Farnesyltransferase, (1994), The Journal of Biological Chemistry, 269, No. 17, pp. 12410–12413.
Reiss, Y. et al., Inhibition of Purified p21ras Farnesyl: Protein Transferase by Cys–AAX Tetrapeptides, (1990), Cell, 62, pp. 81–88.
Reiss, Y. et al., Sequence requirement for peptide recognition by rat brain p21 ras protein farnesyltransferase, (1991), Proc. Natl. Acad. Sci. USA, 88, pp. 732–736.
Schaber, M. D. et al., Polyisoprenylation of Ras in Vitro by a Farnesyl-Protein Transferase, (1990), The Journal of Biological Chemistry, 265, No. 25, pp. 14701–14704.

*Primary Examiner*—Cecilia Tsang
*Attorney, Agent, or Firm*—David A. Muthard; Mark R. Daniel; Joseph F. DiPrima

[57] ABSTRACT

The present invention is directed to compounds which inhibit farnesyl-protein transferase (FPTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

5 Claims, No Drawings

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171-286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583-586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093-1098 (1989); Hancock et al., *Cell* 57:1167-1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., *ibid;* Casey et al., *ibid;* Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell,* 62:81-88 (1990); Schaber et al., *J. Biol. Chem.,* 265:14701-14704 (1990); Schafer et al., *Science,* 249:1133-1139 (1990); Manne et al., *Proc. Natl. Acad. Sci USA.,* 87:7541-7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630-6634(1989)). Cytosol localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., *ibid;* Reiss et. al., *ibid;* Reiss et al., *PNAS,* 88:732-736 (1991)). Such inhibitors may inhibit while serving as alternate substrates for the Ras farnesyl-transferase enzyme, or may be purely competitive inhibitors (U.S. Pat. No. 5,141,851, University of Texas).

Inhibitors of farnesyl protein transferase which are citraconic acid derivatives have been isolated as fermentation products from a strain of *Chaetomella acutiseta* (U.S. Pat. No. 5,260,465 and EP-47671-A). Synthetic analogs of those compounds have also been described (U.S. Pat. Nos. 5,245,061 and 5,260,479).

It is, therefore, an object of this invention to develop non-peptide compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes substituted phenol analogs which inhibit farnesyl-protein transferase and the farnesylation of the oncogene protein Ras, chemotherapeutic compositions containing the compounds of this invention, and methods for producing the compounds of this invention.

The compounds of this invention are illustrated by the following formula:

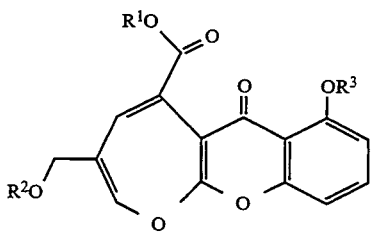

I

DETAILED DESCRIPTION OF THE INVENTION

The compounds of this invention are useful in the inhibition of farnesyl-protein transferase. In a first embodiment of this invention, the inhibitors of farnesyl-protein transferase are illustrated by the formula I:

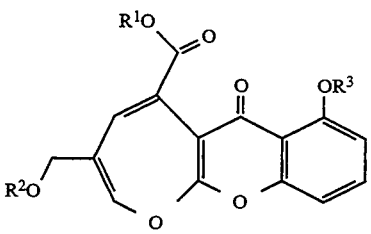

I $R^1$ is hydrogen or $C_{1-4}$ alkyl; and $R^2$ and $R^3$ are independently selected from hydrogen, $C_{1-4}$ alkyl or acetyl or the pharmaceutically acceptable salt thereof.

The following are specific examples of the compounds of the instant invention. Compound 1, 7-hydroxy-3-(hydroxymethyl)-6-oxo-6H-oxepino[2,3-b][1]benzopyran-5-carboxylic acid methyl ester, has been given the trivial name of fusidienol.

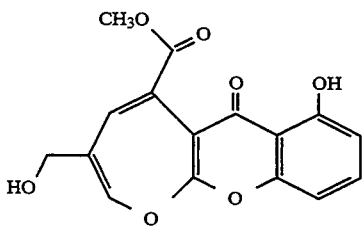

1

Compound 2, 7-acetyloxy-3-[(acetyloxy)methyl]-6-oxo-6H-oxepino[2,3-b][1]benzopyran-5-carboxylic acid methyl ester, has been given the trivial name of diacetylfusidienol.

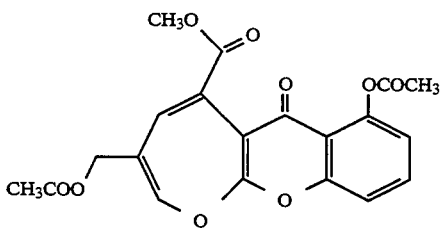

2

In the compounds of the present invention, combinations of substituents/or variables are permissible only if such combinations result in stable compounds.

As used herein, "alkyl" is intended to include both branched and straight-chain saturated aliphatic hydrocarbon groups having the specified number of carbon atoms. The term "alkyl" includes methyl, ethyl, propyl, iso-propyl, butyl, sec-butyl, tert-butyl and the like.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compound 1 is prepared in an aerobic fermentation procedure employing a novel culture, MF5695, identified as *Fusidium griseum*. Although the use of this organism is specifically described herein, mutants of the above described organism are also capable of producing the compounds of this invention.

The culture MF5695 is that of a fungus, *Fusidium griseum*, isolated from leaf litter of a hardwood forest near Lansing, Mich. This culture has been deposited with the American Type Culture Collection at 12301 Parklawn Drive, Rockville, Md. 20852 as ATCC 74265.

The culture MF5695, identified as *Fusidium griseum*, exhibits the following morphological features:

Colonies growing moderately fast on oatmeal agar (Tuite, J. 1968. Plant Pathological Methods. Burgess Publishing Co., Minneapolis, medium no. 159, pg. 51). 25° C., 12 hr photoperiod, after 21 days attaining 47–55 mm in diameter, slightly raised to irregular, velvety to lanose, zonate, with distinct tufts or stromatic mycelial masses towards the center, with stromatic masses up to 1 mm in diameter, margin undulating, submerged, at first translucent to white, soon pale olivaceous buff, Pale Olive-Buff (capitalized color names from Ridgway, R. 1912. Color Standards and Nomenclature, Washington, D.C.), to gray, Light Mineral Gray, Mineral Gray, Storm Gray, or grayish black, Castor Gray. Reverse dull yellowish olive to olivaceous gray, with some radial splitting of medium. Exudates absent. Odor not distinct.

Colonies growing slowly on YME agar (Difco Laboratories), 25° C., 12 hr photoperiod, after 21 days attaining 14–15 mm in diameter, mostly submerged to appressed, irregularly lobed and furrowed, with scant tufts of conidiophores near the inoculation point, translucent to pale buff, with translucent to white conidial tufts. Reverse translucent to pale buff. Exudates absent. Odor not distinct.

Mycelium on YME at 37° C. barely growing submerged in the agar.

Conidiophores micronematous to semi-macronematous, arising at more-or-less right angles from prostrate hyphae on agar surface, abundant, solitary, fasciculate, or loosely aggregated in conidial pustules, 30–60 μm tall, 2–4 μm wide at the base, septate, thin-walled, unbranched or terminating in cells with 2–3 lateral branches. Conidiogenous cells holoblastic, with each conidium giving rise to the next in acropetal succession, accumulating erect chains of conidia, with chains unbranched or rarely branched. Conidia aseptate, smooth, thin-walled, 14–17 μm long, 2–3.5 μm wide, with bases and apices slightly truncate due to secessional scars, with 2–3 scars if conidium was a branch point. Chlamydospores not observed. Hyphae septate, branched, hyaline to pale olivaceous gray in age.

Because this fungal culture produces only simple holoblastic conidia from relatively undifferentiated conidiophores, it is classified among the Hyphomycetes of the Deuteromycotina. The simple conidiophores that give rise to sparsely branched chains of conidia in acropetal succession are characteristic of several genera of Hyphomycetes found in decomposing leaves, such as *Cladosporium, Hyalodendron, Polyscytalum,* and *Fusidium*. The hyaline, aseptate conidia and aggregates of simple conidiophores are characteristic of the genus *Fusidium*. Descriptions of cultural characteristics of *Fusidium griseum* are not available in the literature. However, the isolate described above conforms closely to the descriptions of *F. griseum* growing on leaves in the field (G. L. Barron. 1968. The Genera of Hyphomycetes from Soil. Williams and Wilkins Co., Baltimore; Ellis, M. B. & Ellis, J. P. 1985. Microfungi on Land Plants, An Identification Handbook. Macmillan Publishing Company, New York).

Compounds of this invention can be obtained by culturing the above noted microorganism in aqueous nutrient media containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (eg. ammonium nitrate, ammonium sulfate, ammonium phosphate, etc.) can also be used. The various sources of nitrogen can be used alone or in combination in amounts ranging between 0.2 to 50 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organism which serves as seed in the production of the active compounds. After inoculation, the flasks are incubated with agitation at temperature ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 22 days. The fermentation is conducted aerobically at temperatures ranging from 20° to 40° C. To obtain optimum results, the temperatures are in the range of 22° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound(s) isolated.

A mixture of an alcoholic solvent and an oxygenated solvent, such as an ester or a ketone, is employed to extract a compound(s) of this invention from the solid fermentation medium.

The mixture is vigorously stirred and filtered, and the filtrate is concentrated under reduced pressure. Water is added to the concentrate and the pH is adjusted to about 3 with a mineral acid. The aqueous concentrate is then repeatedly extracted with a water immiscible oxygenated solvent. The water immiscible organic layer is removed and evaporated to dryness. The residue is then generally subjected to several separation steps such as adsorption and partition chromatography, and precipitation. For each separation step, fractions are collected and combined based on results from an assay and/or HPLC/TLC analysis.

The preferred solvent for extraction of the solid fermentation is a 1:1 mixture of methanol and 2-butanone. After concentrating the initial extract and diluting with water, the preferred partitioning solvent is dichloromethane.

The chromatographic separations may be carried out by employing conventional column chromatography with ionic or nonionic absorbents or resins. Silica gel, such as that available from E. Merck, is the preferred adsorbent. When silica gel is the adsorbent, an alcohol/chlorohydrocarbon/organic acid mixture such as methanol/chloroform/acetic acid/water is useful as an eluant. For reverse phase chromatography, the preferred adsorbent is a C8 bonded phase silica gel. The preferred eluant for reverse phase chromatography is a mixture of acetonitrile and water buffered at a low pH, such as 0.1% phosphoric acid, or trifluoroacetic acid. Ionic resins such as Dowex-1 ($Cl^-$) or Dowex-50 ($Ca^{++}$) are also useful in the purification.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, or both of the carboxyl groups are in the salt form.

The intrinsic farnesyl-protein transferase (FPTase) activity of representative compounds of this invention was measured by the assay as described below:

Farnesyl-protein transferase (FPTase) from bovine brain was chromatographed on DEAE-Sephacel (Pharmacia, 0–0.8M NaCl gradient elution), N-octyl agarose (Sigma, 0–0.6M NaCl gradient elution), and a mono Q HPLC column (Pharmacia, 0–0.3M NaCl gradient). Ras-CVLS (Cys-Val-Leu-Ser) at 3.5 mM, 0.25 mM [$^3$H]FPP, and the indicated compounds were incubated with this partially purified enzyme preparation. The FPTase inhibition data presented below is a measurement of the ability of the test compound to inhibit Ras farnesylation in vitro.

Inhibitory activity of the compounds of the instant invention may also be measured with an assay employing the recombinant human FPTase obtained as described by C. A. Omer et al. (*Biochemistry*, 32:5167–5176 (1993)).

The pharmaceutical compositions containing the compounds of structural formula I inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice.

The compounds can be administered orally or parenterally, including intravenous, intramuscular, intraperitoneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carders which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

The compounds of this invention may also be prepared according to the reactions as shown in the Reaction Schemes below, in addition to other standard manipulations such as ester hydrolysis, cleavage of protecting groups, etc., as may be known in the literature or exemplified in the experimental procedures.

REACTION SCHEME A

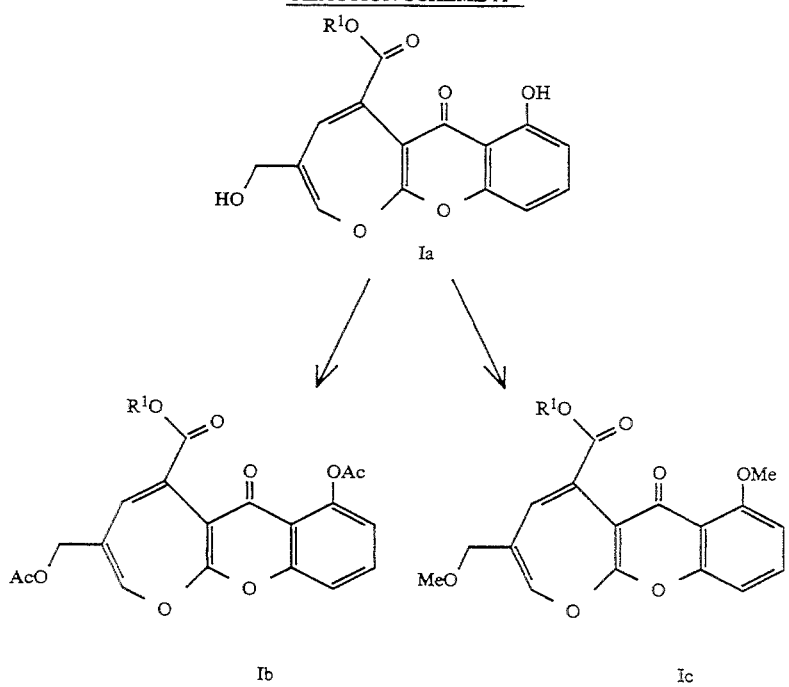

Synopsis of Reaction Scheme A:

The phenyl ring of the compounds of the instant invention may be derivatized as illustrated in Reaction Scheme A. The diol Ia obtained by the fermentation described herein above is acylated under standard conditions, such as acetic anhydride in pyridine, acetyl chloride in pyridine and the like, to provide the bis acylated compound Ib. Treatment of the diol Ia with a methylating reagent, such as diazomethane and the like, provides the monomethyl ether Ic.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch.

When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of Compound 1 by Fermentation

A. Culturing MF5695

MF5695 cultures were maintained as mixtures of spores and hyphae in sterile soil and stored at 4° C. until ready for use. Seed cultures were inoculated by using a small portion of the preserved soil aseptically transferred into a 250 mls Erlenmeyer flask containing 50 mls of seed medium of the following composition (in g/liter); corn steep liquor, 5.0; tomato paste, 40.0; oat flour, 10.0; glucose, 10.0; and trace elements solution, 10 ml/liter (consisting of, in g/liter: $FeSO_4.7H_2O$, 1.0; $MnSO_4.4H_2O$, 1.0; $CuCl_2.2H_2O$, 0.025; $CaCl_2.2H_2O$, 0.1; $H_3BO_3$, 0.056; $(NH_4)_6MoO_{24}.4H_2O$, 0.019; $ZnSO_4.7H_2O$, 0.2; dissolved in 0.6N HCl). The pH of the medium was adjusted to 6.8 by addition of NaOH before sterilization. Seed medium was prepared using distilled water and was dispensed into Erlenmeyer flasks that were capped with cotton plugs before being autoclaved at 121° C. for 20 minutes. Seed cultures were incubated at 25° C., on a gyrotory shaker (220 rpm, 5.1 cm throw) for 72-73 hours prior to inoculation of fermentation flasks.

Fermentations were performed on solid substrate production medium formulated as follows: millet, 15.0 g/250 ml Erlenmeyer flask to which was added 15 mls of 0.5 g yeast extract, 0.1 g sodium tartrate, 0.5 g sucrose, 0.5 g alfalfa, 0.1 ml corn oil, 0.01 g $FeSO_4.7H_2O$. Solid substrate production flasks were capped with cotton plugs and sterilized at 121° C. for 15 minutes. Immediately prior to inoculation, distilled water (15.0 mls) was added to each flask, and the flasks were resterilized at 121° C. for 20 minutes, and then cooled. Each production flask was inoculated with 2.0 ml vegetative seed growth mixed throughout the solid substrate. Production flasks were incubated without agitation at 25° C. for 11 days. An individual flask was extracted with 50 mls MEK to determine its FPTase inhibitory activity. The isolation batch was delivered unextracted.

B. Isolation of Compound 1

The solid state fermentation (MF5695) of *Fusidium griseum* (3.4 L) was grown for 11 days and extracted with methyl ethyl ketone (4.5 L) by shaking the flasks for 2 hrs on a shaker. The extract was collected by filtration through a bed of Celite. Methyl ethyl ketone was removed under reduced pressure by distillation using a rotatory evaporator and finally lyophilized to give oily residue (23.0 gm). This extract was suspended in 20% aqueous-methanol (500 mL) and washed with hexane (2×500 mL). The aqueous-methanol layer was adjusted to 50% aqueous-methanol by addition of 300 mL water and extracted with methylene chloride (2×600 mL). The aqueous-methanol layer was readjusted to water-methanol (3:2) and extracted with ethyl acetate (2×400 mL). Most of the Ras FPTase activity was concentrated in the methylene chloride extract which was concentrated to dryness under reduced pressure to give 4.5 gm material. This was dissolved in 10 mL methylene chloride and was filtered through a 3 cm bed of silica gel in a 600 mL sintered glass funnel. The silica gel bed was washed, after loading the material, with 10% acetone-hexane (250 mL) and elution with 20% acetone-hexane gave a 300 mg fraction which was highly enriched with 1. Crystallization of a small portion of the enriched fraction from methanol gave slightly yellowish crystals of Compound 1; mp. 168°-70° C.

Spectral Data of Compound 1:

$^1H$ NMR ($CD_3OD$, δ): 3.79 (3H, s), 4.14 (2H, d, J=1.5 Hz), 6.57 (1H, t, J=1.5 Hz), 6.82 (1H, dd, J=9.0, 0.5 Hz), 6.95 (1H, dd, J=9.0, 0.5 Hz), 7.06 (1H, s), 7.60 (1H, t, J=8.5 Hz);

$^{13}C$ NMR ($CD_3OD$, δ): 52.90 ($CH_3$), 60.72 ($CH_2$), 105.80 (qC), 108.11 (CH), 110.28 (qC), 113.37 (CH), 131.31 (qC), 131.34 (qC), 134.64 (CH), 136.94 (CH), 145.75 (CH), 155.16 (qC), 161.94 (qC), 164.42 (qC), 168.51 (qC), 183.95 (qC).

UV: ($\lambda_{max}$) ($CH_3CN$-$H_2O$): 230, 330 nm;

IR (ZnSe): 3500, 2953, 1724, 1651, 1610, 1468, 1421, 1361, 1274, 1231, 1176, 1140, 1063, 1020, 896, 816,766 $cm^{-1}$;

HREIMS (m/z): 316.0600 (M+,calcd. for $C_{16}H_{12}O_7$: 316.0583).

EXAMPLE 2

Synthesis of Compound 2:

To a solution of Compound 1 (3 mg) in 0.2 mL anhydrous pyridine was added acetic anhydride (0.2 mL) and the reaction mixture was stirred at room temperature for 48 hrs. Exess of the reagent was destroyed by addition of methanol and volatile materials were evaporated under stream of nitrogen. The product was purified on a Whatman -ODS-3 C-18 (9.4×250 mm) column and eluted, at a flow rate of 4 mL per minutes, with 50% aqueous-acetonitrile containing 0.2% trifluoroacetic acid and fractions lyophilized to give diacetate 2 as an amorphous hint yellow solid.

Spectral data of Compound 2:

$^1H$ NMR ($CD_3OD$+$CDCl_3$, δ): 2.04 (3H, s), 2.34 (3H, s), 3.79 (3H, s), 4.67 (2H, s), 6.63 (1H, s), 7.05 (1H, d, J=8.0 Hz), 7.22 (1H, s), 7.30 (1H, d, J=8.0 Hz), 7.64 (1H, t, J=8.5 Hz).

HREIMS (m/z): 400.0799 (M+, calcd. for $C_{20}H_{16}O_9$: 400.0794), 358.0693 (calcd. for $C_{18}H_{14}O_8$: 358.0689), 342.0743 (calcd. for $C_{18}H_{14}O_7$: 342.0740), 326.0430 (calcd. for $C_{17}H_{10}O_7$: 326.0427), 310.0485 (calcd. for $C_{17}H_{10}O_7$: 310.0477), 298.0484 (calcd. for $C_{16}H_{10}O_6$: 298.0477), 284.0313 (calcd. for $C_{15}H_8O_7$: 284.0321), 266.0198 (calcd. for $C_{15}H_6O_5$: 266.0215), 228.0433 (calcd. for $C_{13}H_8O_4$: 228.0423), 163.0403 (calcd. for $C_9H_7O_3$: 163.0395), 137.0241 (calcd. for $C_7H_5O_3$: 137.0239).

EXAMPLE 3

In Vitro Inhibition of Ras Farnesyl-Protein Transferase

Assays of farnesyl-protein transferase. Partially purified bovine FPTase and Ras peptides (Ras-CVLS, Ras-CVIM and RAS-CAIL) were prepared as described by Schaber et al. *J. Biol. Chem.* 265:14701-14704 (1990) and Gibbs et al. *PNAS U.S.A.* 86:6630-6634 (1989), respectively. Bovine FPTase was assayed in a volume of 100 gl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3H$]-farnesyl diphosphate ([$^3H$]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach H cell harvestor, washed with 100% ethanol, dried and counted in an LKB β-plate counter. The assay was linear with respect to both substrates, FPTase levels and time; less than 10% of the [³H]-FPP was utilized during the reaction period. Purified compounds were dissolved in 100% dimethyl sulfoxide (DMSO) and were diluted 20-fold into the assay. Percentage inhibition is measured by the amount of incorporation of farnesyl in the presence of the test compound when compared to the amount of incorporation in the absence of the test compound. Results are shown in Table 1.

Human FPTase was prepared as described by Omer et al. *Biochemistry* 32:5167–5176 (1993). Human FPTase activity was assayed as described above with the exception that 0.1% (w/v) polyethylene glycol 20,000, 10 μM ZnCl₂ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

TABLE 1

Inhibition of RAS farnesylation by compounds of this invention*

| Compound | IC$_{50}$ (nM)* | |
| --- | --- | --- |
| | bovine | human |
| 1 | 300 | 2700 |
| 2 | 1000 | n.a. |

*(IC$_{50}$ is the concentration of the test compound which gives 50% inhibition of FPTase under the described assay conditions)

n.a. = not available

What is claimed is:

1. A compound which inhibits farnesyl-protein transferase of the formula I:

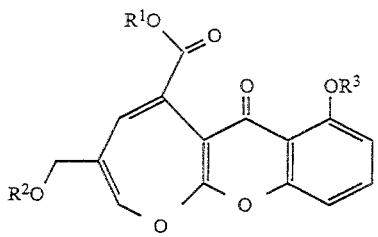

R¹ is hydrogen or C$_{1-4}$ alkyl; and
R² and R³ are independently selected from hydrogen, C$_{1-4}$ alkyl or acetyl
or the pharmaceutically acceptable salt thereof.

2. The compound according to claim 1 which is:
7-hydroxy-3-(hydroxymethyl)-6-oxo-6H-oxepino[2,3-b][1]benzopyran-5-carboxylic acid methyl ester

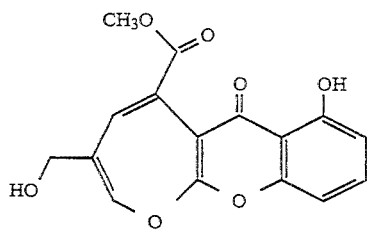

3. The compound according to claim 1 which is:
7-acetyloxy-3-[(acetyloxy)methyl]-6-oxo-6H-oxepino[2,3-b][1]benzopyran-5-carboxylic acid methyl ester

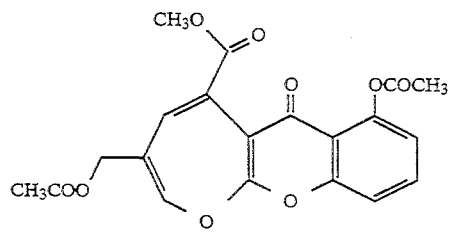

4. A pharmaceutical composition useful for inhibiting farnesyl protein transferase comprising a pharmaceutical carrier, and dispersed therein, a therapeutically effective amount of a compound of claim 1.

5. A pharmaceutical composition useful for inhibiting farnesyl protein transferase comprising a pharmaceutical carrier, and dispersed therein, a therapeutically effective amount of a compound of claim 2.

* * * * *